(12) United States Patent
Gou

(10) Patent No.: US 10,820,805 B2
(45) Date of Patent: Nov. 3, 2020

(54) HEAD-MOUNTED MAGNETIC RESONANCE IMAGING DEVICE AND DEMENTIA MONITORING SYSTEM

(71) Applicant: HON HAI PRECISION INDUSTRY CO., LTD., New Taipei (TW)

(72) Inventor: Tai-Ming Gou, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 323 days.

(21) Appl. No.: 16/015,522

(22) Filed: Jun. 22, 2018

(65) Prior Publication Data

US 2019/0269330 A1 Sep. 5, 2019

Related U.S. Application Data

(60) Provisional application No. 62/363,861, filed on Mar. 1, 2018.

(51) Int. Cl.
*A61B 5/00* (2006.01)
*G01R 33/34* (2006.01)
*G01R 33/38* (2006.01)
*A61B 5/055* (2006.01)

(52) U.S. Cl.
CPC .......... *A61B 5/0042* (2013.01); *A61B 5/0013* (2013.01); *A61B 5/0022* (2013.01); *A61B 5/055* (2013.01); *A61B 5/6803* (2013.01); *G01R 33/34084* (2013.01); *G01R 33/3802* (2013.01); *A61B 2576/026* (2013.01)

(58) Field of Classification Search
None
See application file for complete search history.

(56) References Cited

U.S. PATENT DOCUMENTS

| 2015/0244665 | A1* | 8/2015 | Choi | H04L 51/24 |
| | | | | 709/206 |
| 2016/0018489 | A1* | 1/2016 | Farivar-Mohseni | ......... |
| | | | | G01R 33/34007 |
| | | | | 600/422 |
| 2016/0155226 | A1* | 6/2016 | Kano | A61B 5/7275 |
| | | | | 382/131 |
| 2017/0322273 | A1* | 11/2017 | Truong | G01R 33/4806 |

* cited by examiner

*Primary Examiner* — Joel F Brutus
(74) *Attorney, Agent, or Firm* — ScienBiziP, P.C.

(57) ABSTRACT

This disclosure relates to a head-mounted magnetic resonance imaging device. The head-mounted magnetic resonance imaging device includes a head-mounted imaging unit, a controlling computer, and a signal processing computer. The signal processing computer includes a controlling module, a data processing module, an image reconstructing module, an image storing module, and an image comparing module. The image reconstructing module forms cross-sectional scanned images of an user's brain memory showing microstructure. The image comparing module is configured to analyze and comparing the cross-sectional scanned images of the user's brain memory showing microstructure collected at different times so that the controlling computer provided user suggestions corresponding to different judgement results of the image comparing module. The system may comprise a dementia monitoring system that provides users with advisory dementia warnings so users may be advised to seek further medical advice.

18 Claims, 7 Drawing Sheets

HEAD-MOUNTED MAGNETIC RESONANCE IMAGING DEVICE AND DEMENTIA MONITORING SYSTEM

CROSS-REFERENCE TO RELATED APPLICATIONS

This application claims the benefit under 35 U.S.C. § 119(c) of U.S. Provisional Application No. 62/636,861 filed Mar. 1, 2018, the disclosure of which is incorporated by reference herein.

BACKGROUND

1. Technical Field

The present disclosure relates to medical equipment technical field, especially, relates to head-mounted magnetic resonance imaging devices and dementia monitoring systems.

2. Description of Related Art

Dementia is a broad category of brain diseases that cause a long-term and often gradual decrease in the ability to think and remember that is great enough to affect a person's daily functioning. Dementia is usually translated as "Shizhizheng" in Taiwan, translated as "Chidaizheng" in Chinese Mainland, and translated as "Tuihuazheng" in Hong Kong. Recently, more and more people suffer a dementia. However, after the patient has been found himself suffer a dementia it can be too late for the patient to receive a treatment.

Therefore, what is needed is equipment for people to detect and predict the dementia so that the patient can go to see a doctor and receive immediate treatment.

BRIEF DESCRIPTION OF THE DRAWINGS

Many aspects of the embodiments can be better understood with reference to the following drawings. The components in the drawings are not necessarily drawn to scale, the emphasis instead being location upon clearly illustrating the principles of the embodiments. Moreover, in the drawings, like reference numerals designate corresponding parts throughout the several views.

DETAILED DESCRIPTION

Figure 1:
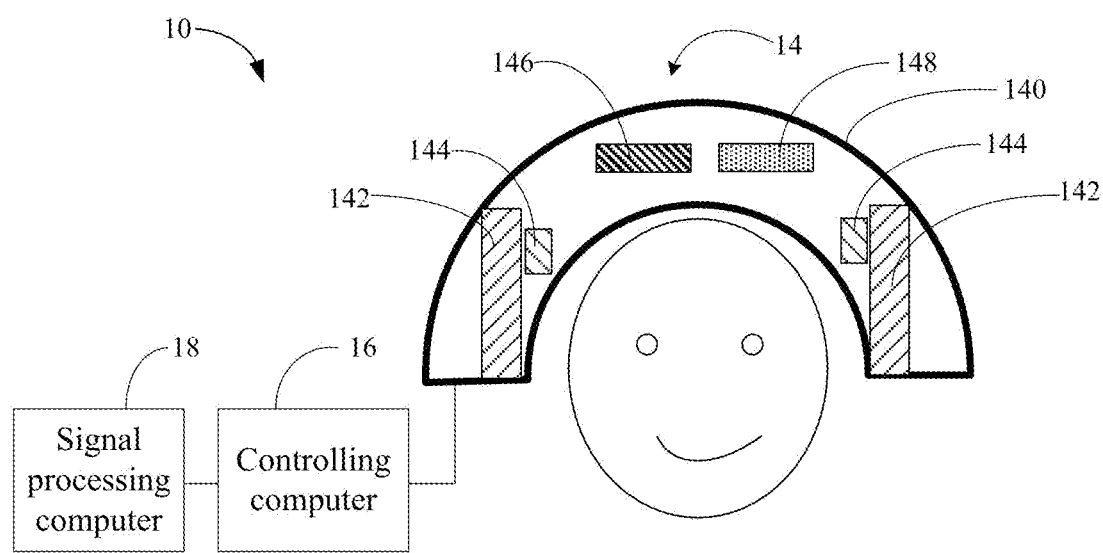
FIG. 1 is a schematic view of one embodiment of a head-mounted magnetic resonance imaging device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale, and the proportions of certain parts may be exaggerated better illustrate details and features. The description is not to considered as limiting the scope of the embodiments described herein.

Several definitions that apply throughout this disclosure will now be presented. The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicates that at least a portion of a region is partially contained within a boundary formed by the object. The term "substantially" is defined to essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

In general, the word "module," as used herein, refers to logic embodied in hardware or firmware, or to a captureion of software instructions, written in a programming language, such as, for example, Java, C, or assembly. One or more software instructions in the modules may be embedded in firmware, such as an EPROM. It will be appreciated that modules may comprise connected logic units, such as gates and flip-flops, and may comprise programmable units, such as programmable gate arrays or processors. The modules described herein may be implemented as either software and/or hardware modules and may be stored in any type of computer-readable medium or other computer storage device.

References will now be made to the drawings to describe, in detail, various embodiments of the present head-mounted magnetic resonance imaging devices and dementia monitoring systems.

Embodiment 1

Referring to FIG. 1, a head-mounted magnetic resonance imaging device 10 of one embodiment is provided. The head-mounted magnetic resonance imaging device 10 includes an imaging unit 14, a controlling computer 16, and a signal processing computer 18. The imaging unit 14 includes a shell 140, and a main magnet 142, a gradient coil 144, a radio frequency coil 146, and a signal receiving system 148 accommodated in the shell 140.

Figure 2:
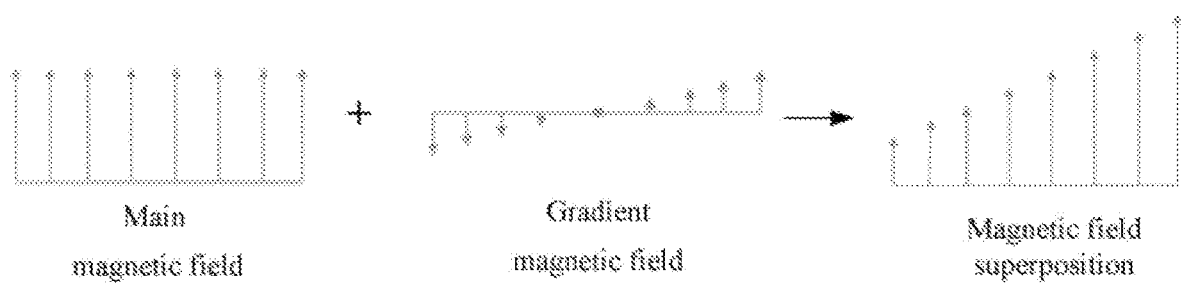
FIG. 2 is schematic view of magnetic field superposition of the main magnetic field and the gradient magnetic field of the head-mounted magnetic resonance imaging device.

The shell 140 is designed to helmet like shape, such as a hemispherical shape, so that the user can wear it on the head in detecting process. The main magnet 142 produces a strong static magnetic field used as the main magnetic field. The direction of the main magnetic field is defined as Z direction. The main magnet 142 can be a permanent magnet or a superconducting coil. The intensity of the main magnetic field is in a range from about 0.5 Tesla to about 3 Tesla. Alternatively, the main magnet 142 can include a compensative coil (not shown) used to makes the static magnetic field being close to the ideal uniform magnetic field. The gradient coil 144 produces a gradient magnetic field, and the directions of the gradient magnetic field are X direction and Y direction. The intensity of the gradient magnetic field is in a range from about ±0.1 Tesla to about ±0.5 Tesla. The X direction and Y direction are perpendicular with each other. A first angle is formed between the X direction and the Z direction, and a second angle is formed between the Y direction and the Z direction. Each of the first angle and the second angle is from about 45 degrees to about 60 degrees, so that the component along the Z direction of the gradient magnetic field and the main magnetic field can have a superposition. As shown in FIG. 2, a non-uniform magnetic field along the Z direction is formed after the superposition of the gradient magnetic field and the main magnetic field. The non-uniform magnetic field is a gradient along the Z direction, so that the layer selection and the position can be achieved. The radio frequency coil 146 produces a radiofrequency magnetic field, so that to cause magnetic resonance signals. The signal receiving system 148 receives the magnetic resonance signals, converts the magnetic resonance signal to a digital signal by a convertor, storings the digital signal in a register, and sends the digital signal to the signal processing computer 18. The structure and location of the main magnet 142, the gradient coil 144, the radio frequency coil 146, and the signal receiving system 148 are not limited and can be designed as needed.

The controlling computer 16 controls the operation of the head-mounted magnetic resonance imaging device 10. The controlling computer 16 can include user interface so that the user can operate the head-mounted magnetic resonance imaging device 10. The controlling computer 16 can also be connected to the mobile electronic device of the user, such as mobile phone, by wires or wireless. Thus, the user can operate the head-mounted magnetic resonance imaging device 10 by downloading an APP by the mobile phone. In operation of the head-mounted magnetic resonance imaging device 10, the imaging unit 14 is worn on the head of the user. The imaging unit 14 generates a uniform main magnetic field around the head of the user and a gradient magnetic field in the main magnetic field. The radio frequency coil 146 generates a radiofrequency magnetic field to cause magnetic resonance signals. The controlling computer 16 can obtain a 2D or 2.5D nuclear magnetic resonance (NMR) image by Fourier transform.

Figure 3:
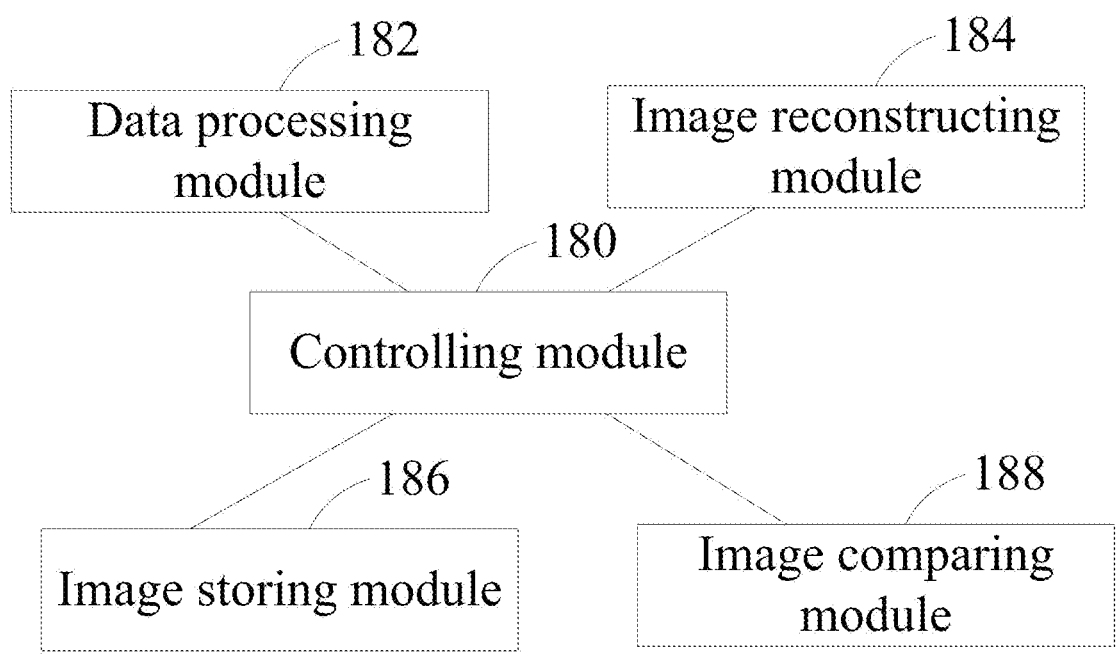
FIG. 3 is a function block diagram of one embodiment of a signal processing computer of the head-mounted magnetic resonance imaging device.

Referring to FIG. 3, in one embodiment, the signal processing computer 18 includes a controlling module 180, a data processing module 182, an image reconstructing module 184, an image storing module 186, and an image comparing module 188. The controlling module 180 is respectively electrically connected to and controls the work of the data processing module 182, the image reconstructing module 184, the image storing module 186, and the image comparing module 188. The data processing module 182 processes the raw data to form a processed data. The image reconstructing module 184 forms magnetic resonance images with different parameters according to the processed data. The image storing module 186 stores the magnetic resonance images. The magnetic resonance images are cross-sectional scanned images of the user's brain memory showing microstructure. The image comparing module 188 analyzes and compare the cross-sectional scanned images of the user's brain memory showing microstructure captured at different times. The controlling computer 16 can output different suggestions, that corresponding to different judgement results of the image comparing module 188, to the user.

In one embodiment, the judgement results of the image comparing module 188 includes three changes levels. Level 1: the cross-sectional scanned images of the user's brain memory showing microstructure captured at different times have no changes. Level 2: the cross-sectional scanned images of the user's brain memory showing microstructure captured at different times have slight changes. Level 3: the cross-sectional scanned images of the user's brain memory showing microstructure captured at different times have obvious changes. The "no changes", "slight changes", and "obvious changes" are determined according to the size changes of the cross-sectional scanned images along a single direction or several different directions. In one embodiment, H1 is defined as a first changes threshold, H2 is defined as a second changes threshold, and H1<H2. When the changes of the cross-sectional scanned images is less than the first changes threshold H1, the judgement is "no changes." When the changes of the cross-sectional scanned images is greater than or equal to the first changes threshold H1 and less than or equal to the second changes threshold H2, the judgement is "slight changes." When the changes of the cross-sectional scanned images is greater than the second changes threshold H2, the judgement is "obvious changes." The first changes threshold H1 and the second changes threshold H2 can be set according to the actual situation. The first changes threshold H1 and the second changes threshold H2 can be a length value or a rate. For example, the first changes threshold H1 is 2-5%, and the second changes threshold H2 is 5%-10%. Namely, the first changes threshold H1 and the second changes threshold H2 are reduction rate. In one embodiment, the size Ln of the cross-sectional scanned image captured in the $n^{th}$ time is compared with the size L1 of the cross-sectional scanned image captured in the first time, "n" is an integer greater than 1. For example, when the condition (L1−Ln)/Ln<2% is met, the judgement is "no changes"; when the condition 2%<(L1−Ln)/Ln<5% is met, the judgement is "slight changes"; when the condition 5%<(L1−Ln)/Ln is met, the judgement is "obvious changes." The size Ln can be a length or width along any direction.

Alternatively, the first change threshold H1 and the second change threshold H2 can be a microstructure characteristic change of the cross-sectional scanned images of the user's brain memory. The image storing module 186 can store the normal microstructure characteristic of the cross-sectional scanned images of the user's brain memory showing as a standard image, such as the shape and texture of the bulges and grooves. The dementia can be predicted by comparing the cross-sectional scanned images of the user's brain memory showing microstructure with the standard image. The threshold can be defined by the image processing software (not shown).

The controlling computer 16 can output different suggestions to the user corresponding to different judgement results of the image comparing module 188. The outputted suggestions can be designed as needed. For example, when the cross-sectional scanned images of the user's brain memory showing microstructure captured at different times have no changes, the outputted suggestion is "You do not have evidence of dementia"; when the cross-sectional scanned images of the user's brain memory showing microstructure captured at different times have slight changes, the outputted suggestion is "You may have dementia, please consult a doctor"; and when the cross-sectional scanned images of the user's brain memory showing microstructure captured at different times have obvious changes, the outputted suggestion is "You appear to have evidence of dementia, please see a doctor immediately." The device should also warn the user that it is not providing medical advice, but merely reacting to certain changes in the user's brain structure, etc.

Figure 4:
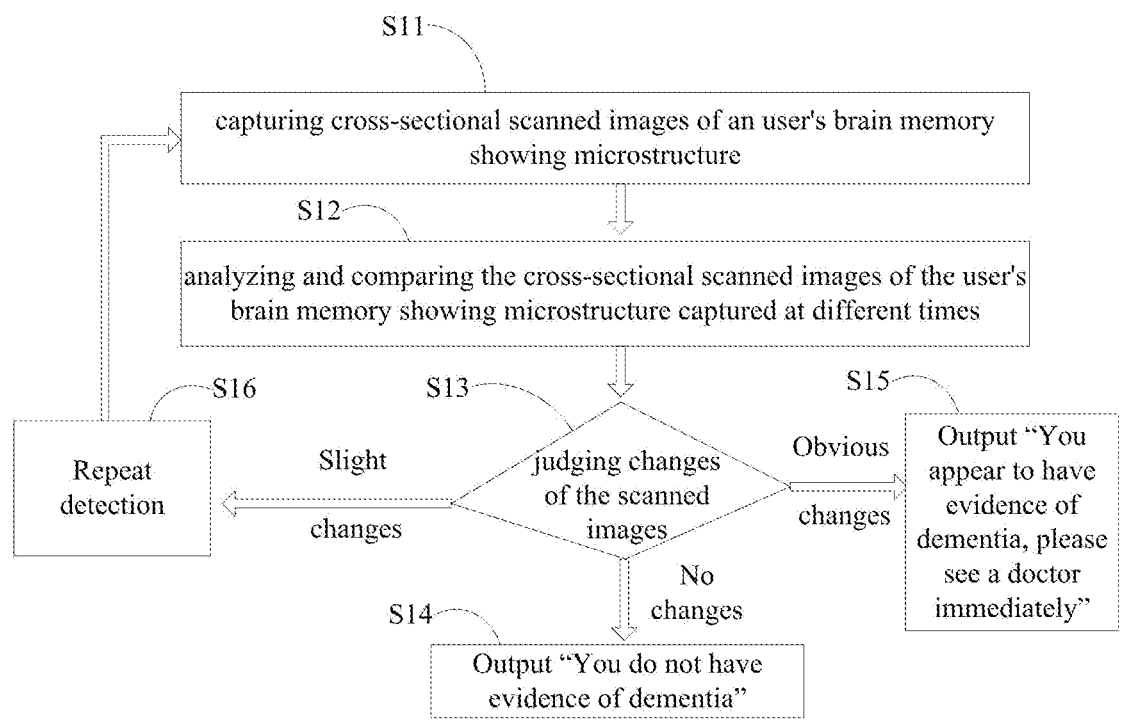
FIG. 4 is a work flow chart of one embodiment of the head-mounted magnetic resonance imaging device.

Referring to FIG. 4, alternatively, when the cross-sectional scanned images of the user's brain memory showing microstructure captured at different times have slight changes, the head-mounted magnetic resonance imaging device 10 can repeat detection. The work method of the head-mounted magnetic resonance imaging device 10 includes following steps:

step (S11), capturing cross-sectional scanned images of an user's brain memory showing microstructure;

step (S12), analyzing and comparing the cross-sectional scanned images of the user's brain memory showing microstructure captured at different times;

step (S13), judging changes of the cross-sectional scanned images, when the judgement is "no changes", go to step (S14), when the judgement is "obvious changes" go to step (S15); when the judgement is "slight changes", go to step (S16);

step (S14), output "You do not have evidence of dementia";

step (S15), output "You appear to have evidence of dementia, please see a doctor immediately"; and step (S16), repeat detection.

In step (S16), when the judgement is still "slight changes" after repeating detection three times, output "You may have dementia, please see a doctor immediately."

Because the dementia may cause the brain memory reduction along any one or more than one directions, the several size Ln along different directions can be used to judge the changes level so that to have an accurate judgement. In one embodiment, the maximum of the changes along different directions of the cross-sectional scanned images is compared with the first changes threshold H1 and the second changes threshold H2, thus the accuracy is improved.

In one embodiment, a plurality of first lengths Lnx along X direction, a plurality of second lengths Lny along Y direction, and a plurality of third lengths Lnz along Z direction, of the cross-sectional scanned image of the user's brain memory showing microstructure are captured. The X direction, the Y direction, and the Z direction are perpendicular with each other. The image comparing module 188 analyzes and compares the cross-sectional scanned images of the user's brain memory showing microstructure by respectively using the first lengths Lnx, the second lengths Lny, and the third lengths Lnz. Thus, a first judgement result along X direction, a second judgement result along Y direction, and a third judgement result along Z direction are obtained. If the three directions have the same judgement result, the same judgement result is used as the final judgement. If any two directions have the same judgement result, the same judgement result of the two directions is used as the final judgement. If the three directions have different judgement results, "slight changes" is used as the final judgement.

Figure 5:
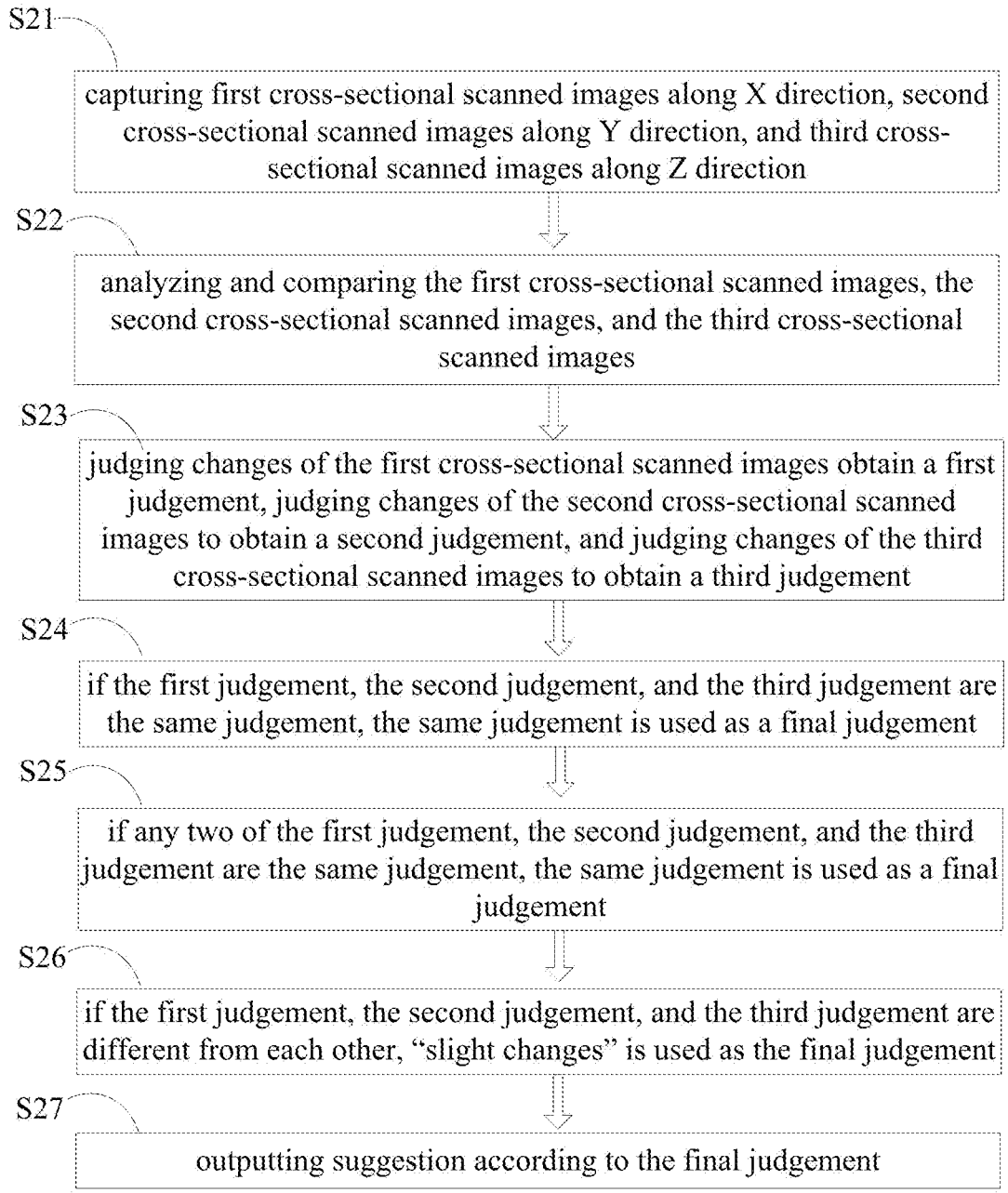
FIG. 5 is a work flow chart of another embodiment of the head-mounted magnetic resonance imaging device.

Referring to FIG. 5, in one embodiment, the work method of the head-mounted magnetic resonance imaging device 10 includes following steps:

step (S21), capturing first cross-sectional scanned images along X direction, second cross-sectional scanned images along Y direction, and third cross-sectional scanned images along Z direction;

step (S22), analyzing and comparing the first cross-sectional scanned images, the second cross-sectional scanned images, and the third cross-sectional scanned images;

step (S23), judging changes of the first cross-sectional scanned images obtain a first judgement, judging changes of the second cross-sectional scanned images to obtain a second judgement, and judging changes of the third cross-sectional scanned images to obtain a third judgement;

step (S24), if the first judgement, the second judgement, and the third judgement are the same judgement, the same judgement is used as a final judgement;

step (S25), if any two of the first judgement, the second judgement, and the third judgement are the same judgement, the same judgement is used as a final judgement;

step (S26), if the first judgement, the second judgement, and the third judgement are different from each other, "slight changes" is used as the final judgement; and step (S27), outputting suggestion according to the final judgement.

In steps (S27), when the final judgement is "no changes", the suggestion is "You do not have evidence of dementia"; when the final judgement is "obvious changes", the suggestion is "You appear to have evidence of dementia, please see a doctor immediately"; when the final judgement is "slight changes", the suggestion is "repeat detection."

In another embodiment, the head-mounted magnetic resonance imaging device 10 has a fast detecting mode and an accurate detecting mode. In the fast detecting mode, only the lengths Ln along a single direction are obtained and used to judge the dementia. In the accurate detecting mode, the plurality of first lengths Lnx along X direction, the plurality of second lengths Lny along Y direction, and the plurality of third lengths Lnz along Z direction are obtained to used judge the dementia. The user can select the work mode of the head-mounted magnetic resonance imaging device 10 as needed.

The head-mounted magnetic resonance imaging device 10 can be installed in a public location, such as a mall or a cafe. The new user can register an account as an ID and login each time. The user can go to the nearest head-mounted magnetic resonance imaging device 10 to take an examination. The user can operate the head-mounted magnetic resonance imaging device 10 by a mobile phone that is connected to the head-mounted magnetic resonance imaging device 10 by wire or wireless. For example, the user can operate the head-mounted magnetic resonance imaging device 10 by scanning the quick response code by the mobile phone. The head-mounted magnetic resonance imaging device 10 can send the suggestion to the mobile phone. The user are also reminded that the test results are only suggestions and not medical advice.

Because dementia mainly causes the deterioration and atrophy of the anterior and posterior frontotemporal lobes, only the NMR images of the anterior and posterior frontotemporal lobes are needed to be monitored. Furthermore, the imaging unit 14 can have no rotator in the process of obtaining 2D NMR images. Thus, the head-mounted magnetic resonance imaging device 10 can have a simple structure and form a compact head-mounted device.

Embodiment 2

Figure 6:
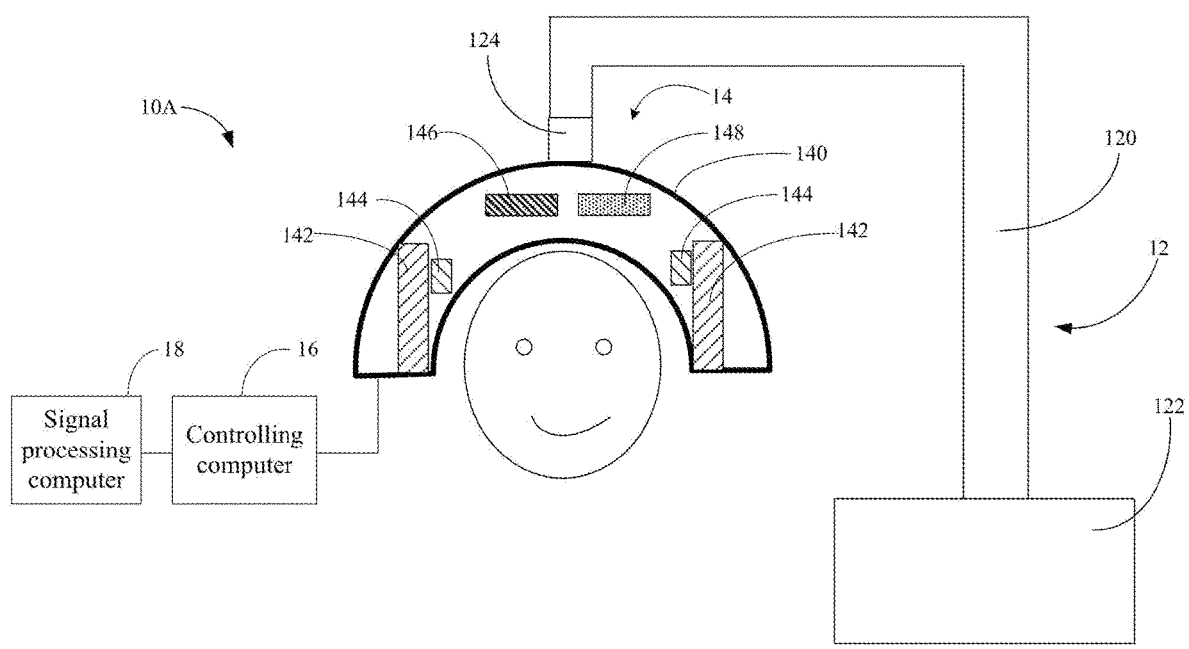
FIG. 6 is a schematic view of another one embodiment of a head-mounted magnetic resonance imaging device.

Referring to FIG. 6, a head-mounted magnetic resonance imaging device 10A of another one embodiment is provided. The head-mounted magnetic resonance imaging device 10A includes a bracket 12, an imaging unit 14, a controlling computer 16, and a signal processing computer 18.

The head-mounted magnetic resonance imaging device 10A of embodiment 2 is similar to the head-mounted magnetic resonance imaging device 10 of embodiment 1, except that the head-mounted magnetic resonance imaging device 10A is rotary type, and further includes the bracket 12.

The bracket 12 includes a support rod 120, a pedestal 122, and a rotator 124. One end of the support rod 120 is fixed on the pedestal 122, and the other end of the support rod 120 is fixed on the rotator 124. The rotator 124 is connected to the shell 140 of the imaging unit 14. The rotator 124 is also connected to the controlling computer 16 by wire or wireless.

In use, the head-mounted magnetic resonance imaging device 10A, the imaging unit 14 is suspended above the head of the user to accommodate the head in the shell 140. The rotator 124 drives the imaging unit 14 to rotate so that to obtain the image of the brain from different angles, thus a 3D nuclear magnetic resonance (NMR) image can be obtained. The support rod 120 and the pedestal 122 are optional, and the bracket 12 can only includes the rotator 124. In uses, the imaging unit 14 is installed on a wall, a roof, or other place of the house by the rotator 124.

Because the 3D NMR image can be obtained, the image comparing module 188 can comparing the volumes of the brain memory showing with a standard volume, such as the anterior and posterior frontotemporal lobes. The image storing module 186 can storing the normal volume of the brain memory showing as the standard volume. The first change threshold H1 and the second change threshold H2 can be a volume change of the brain memory showing. The volume changes between the first change threshold H1 and the second change threshold H2 can be a ratio change or quantity change.

Embodiment 3

Figure 7:
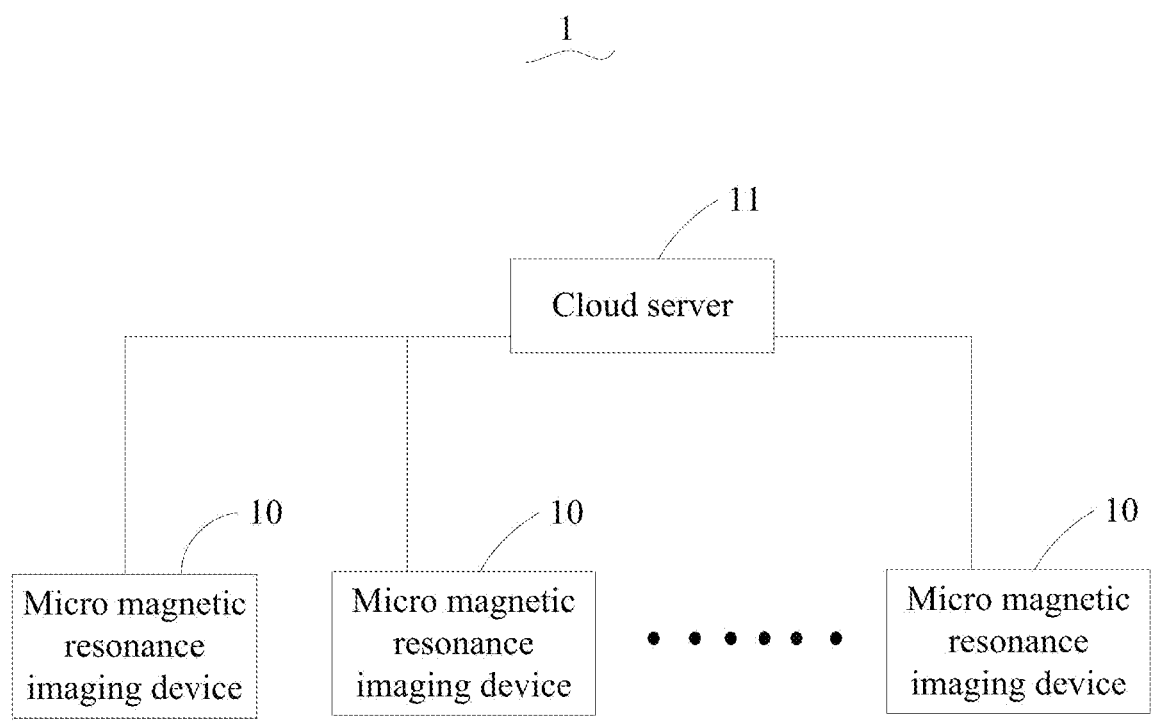
FIG. 7 is a function block diagram of one embodiment of a dementia monitoring system using the head-mounted magnetic resonance imaging devices above.

Referring to FIG. 7, a dementia monitoring system 1 of embodiment 4 is provided. The dementia monitoring system 1 includes a plurality of head-mounted magnetic resonance imaging devices 10 located in different locations and a cloud server 11 electrically connected to the plurality of head-mounted magnetic resonance imaging devices 10 by wires or wireless. The plurality of head-mounted magnetic resonance imaging devices 10 is configures to capture cross-sectional scanned images of an user's brain memory showing microstructure and send the cross-sectional scanned images to the cloud server 11. The cloud server 11 is configures to store, analysis, and compare the cross-sectional scanned images of the user's brain memory showing microstructure captured at different times. The cloud server 11 also sends the judgement results to the mobile electronic devices such as mobile phone.

The dementia monitoring system 1 allows the user to select the nearest head-mounted magnetic resonance imaging device 10 for imaging, so that the user does not have to always go to the same location. The head-mounted magnetic resonance imaging device 10 can also be replaced by the head-mounted magnetic resonance imaging devices 10A, 10B.

Alternatively, because the cloud server 11 plays the functions of analyzing and comparing the cross-sectional scanned images, each of the plurality of head-mounted magnetic resonance imaging devices 10 can only include the carrying unit 12, the imaging unit 14, and the controlling computer 16 and have not any signal processing computer 18.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A head-mounted magnetic resonance imaging device, comprising:
    a head-mounted imaging unit
    a controlling computer;
    a signal processing computer, the signal processing computer comprises a controlling module, a data processing module, an image reconstructing module, and an image storing module; and the image reconstructing module form cross-sectional scanned images of an user's brain memory showing microstructure; and
    a bracket, the bracket comprises a support rod, a pedestal, and a rotator; one end of the support rod is fixed on the pedestal, and the other end of the support rod is fixed on the rotator; and the rotator is connected to a shell of the head-mounted imaging unit,
    wherein the signal processing computer further comprises an image comparing module, the image comparing module is configured to analyze and comparing the cross-sectional scanned images of the user's brain memory showing microstructure collected at different times, and the controlling computer shows different user suggestions corresponding to or depending on different judgement results of the image comparing module.

2. The head-mounted magnetic resonance imaging device as claimed in claim 1, wherein the imaging unit comprises a shell, a main magnet, a gradient coil, a radio frequency coil, and a signal receiving system accommodated in the shell.

3. The head-mounted magnetic resonance imaging device as claimed in claim 1, wherein the controlling computer comprises a user interface.

4. The head-mounted magnetic resonance imaging device as claimed in claim 1, wherein the controlling computer is connected to a mobile electronic device of the user, whereby a user operates the head-mounted magnetic resonance imaging device by downloading and using an application.

5. The head-mounted magnetic resonance imaging device as claimed in claim 1, wherein the judgement results comprises at least three change levels:
    the cross-sectional scanned images of the user's brain memory showing microstructure captured at different times have no changes;
    the cross-sectional scanned images of the user's brain memory showing microstructure captured at different times have slight changes; and the cross-sectional scanned images of the user's brain memory showing microstructure captured at different times have changes.

6. The head-mounted magnetic resonance imaging device as claimed in claim 5, wherein H1 is defined as a first change threshold, H2 is defined as a second change threshold, and H1<H2;

the changes of the cross-sectional scanned images is less than the first changes threshold H1, the judgement is no changes;

the changes of the cross-sectional scanned images is greater than or equal to the first changes threshold H1 and less than or equal to the second changes threshold H2, the judgement is slight changes;

the changes of the cross-sectional scanned images is greater than the second changes threshold H2, the judgement is changes.

7. The head-mounted magnetic resonance imaging device as claimed in claim 1, further comprising a rotator, and the rotator is connected to a shell of the head-mounted.

8. The head-mounted magnetic resonance imaging device as claimed in claim 1, wherein a work method of the head-mounted magnetic resonance imaging device comprises:

step (S11), capturing cross-sectional scanned images of the user's brain memory showing microstructure;

step (S12), analyzing and comparing the cross-sectional scanned images of the user's brain memory showing microstructure captured at different times;

step (S13), judging changes of the cross-sectional scanned images, when the judgement is no changes, go to step (S14), when the judgement is changes go to step (S15); the judgement is slight changes, go to step (S16);

step (S14), outputting You do not have evidence of dementia;

step (S15), outputting You appear to have evidence of dementia, please see a doctor immediately; and step (S16), repeat detection.

9. The head-mounted magnetic resonance imaging device as claimed in claim 8, wherein the work method of the head-mounted magnetic resonance imaging device comprises:

capturing first cross-sectional scanned images along X direction, second cross-sectional scanned images along Y direction, and third cross-sectional scanned images along Z direction;

analyzing and comparing the first cross-sectional scanned images, the second cross-sectional scanned images, and the third cross-sectional scanned images;

judging changes of the first cross-sectional scanned images obtain a first judgement, judging changes of the second cross-sectional scanned images to obtain a second judgement, and judging changes of the third cross-sectional scanned images to obtain a third judgement;

the first judgement, the second judgement, and the third judgement are the same judgement, the same judgement is used as a final judgement;

any two of the first judgement, the second judgement, and the third judgement are the same judgement, the same judgement is used as a final judgement;

the first judgement, the second judgement, and the third judgement are different from each other, slight changes is used as the final judgement; and outputting suggestion according to the final judgement.

10. A dementia monitoring system, comprising:

a plurality of head-mounted magnetic resonance imaging devices, wherein each of the plurality of head-mounted magnetic resonance imaging devices comprises:
a head-mounted imaging unit;
a controlling computer;
a support rod;
a pedestal; and
a rotator,
wherein one end of the support rod is fixed on the pedestal, and the other end of the support rod is fixed on the rotator; and the rotator is connected to a shell of the head-mounted imaging unit, a cloud server connected to the plurality of head-mounted magnetic resonance imaging devices, wherein the cloud server comprises:
a controlling module;
a data processing module;
an image reconstructing module, the image reconstructing module form cross-sectional scanned images of an user's brain memory showing microstructure;
an image storing module; and
an image comparing module, wherein the image comparing module is configured to analyze and compare the cross-sectional scanned images of the user's brain memory showing microstructure collected at different times, and the cloud server sends, different user suggestions, corresponding to different judgement results of the image comparing module, to a user's mobile electronic device.

11. The dementia monitoring system as claimed in claim 10, wherein the imaging unit comprises a shell, a main magnet, a gradient coil, a radio frequency coil, and a signal receiving system accommodated in the shell.

12. The dementia monitoring system as claimed in claim 10, wherein the controlling computer comprises a user interface.

13. The dementia monitoring system as claimed in claim 10, wherein the controlling computer is connected to a mobile electronic device of the user by wires or wireless, so that the user operates the head-mounted magnetic resonance imaging device by downloading an application.

14. The dementia monitoring system as claimed in claim 10 wherein the judgement results comprises at least three change levels:

the cross-sectional scanned images of the user's brain memory showing microstructure captured at different times have no changes;

the cross-sectional scanned images of the user's brain memory showing microstructure captured at different times have slight changes; and the cross-sectional scanned images of the user's brain memory showing microstructure captured at different times have changes.

15. The dementia monitoring system as claimed in claim 14, wherein H1 is defined as a first change threshold, H2 is defined as a second change threshold, and H1<H2;

the changes of the cross-sectional scanned images is less than the first changes threshold H1, the judgement is no changes;

the changes of the cross-sectional scanned images is greater than or equal to the first changes threshold H1 and less than or equal to the second changes threshold H2, the judgement is slight changes;

the changes of the cross-sectional scanned images is greater than the second changes threshold H2, the judgement is changes.

16. The dementia monitoring system as claimed in claim 10, wherein the head-mounted magnetic resonance imaging device further comprises a rotator, and the rotator is connected to a shell of the head-mounted imaging unit.

17. The dementia monitoring system as claimed in claim 10, wherein a work method of the dementia monitoring system comprises:
- step (S11), capturing cross-sectional scanned images of the user's brain memory showing microstructure;
- step (S12), analyzing and comparing the cross-sectional scanned images of the user's brain memory showing microstructure captured at different times;
- step (S13), judging changes of the cross-sectional scanned images, when the judgement is no changes, go to step (S14), when the judgement is great changes go to step (S15); when the judgement is slight changes, go to step (S16);
- step (S14), sending You do not have evidence of dementia to the mobile electronic device;
- step (S15), sending You appear to have evidence of dementia, please see a doctor immediately to the mobile electronic device; and
- step (S16), sending Repeat detection to the mobile electronic device.

18. The dementia monitoring system as claimed in claim 17, wherein the work method of the dementia monitoring system comprises:
- capturing first cross-sectional scanned images along X direction, second cross-sectional scanned images along Y direction, and third cross-sectional scanned images along Z direction;
- analyzing and comparing the first cross-sectional scanned images, the second cross-sectional scanned images, and the third cross-sectional scanned images;
- judging changes of the first cross-sectional scanned images obtain a first judgement, judging changes of the second cross-sectional scanned images to obtain a second judgement, and judging changes of the third cross-sectional scanned images to obtain a third judgement;
- the first judgement, the second judgement, and the third judgement are the same judgement, the same judgement is used as a final judgement;
- any two of the first judgement, the second judgement, and the third judgement are the same judgement, the same judgement is used as a final judgement;
- the first judgement, the second judgement, and the third judgement are different from each other, slight changes is used as the final judgement; and
- sending a suggestion according to the final judgement.

\* \* \* \* \*

UNITED STATES PATENT AND TRADEMARK OFFICE
CERTIFICATE OF CORRECTION

PATENT NO. : 10,820,805 B2
APPLICATION NO. : 16/015522
DATED : November 3, 2020
INVENTOR(S) : Tai-Ming Gou Page 1 of 1

It is certified that error appears in the above-identified patent and that said Letters Patent is hereby corrected as shown below:

On the Title Page

Please replace Item (60) regarding "Provisional application No.62/363,861 filed on Mar. 1, 2018" with the following:
Provisional application No. 62/636,861 filed on Mar. 1, 2018

Signed and Sealed this
Twelfth Day of January, 2021

Andrei Iancu
*Director of the United States Patent and Trademark Office*